United States Patent
Burgos

Patent Number: 5,810,710
Date of Patent: Sep. 22, 1998

[54] DISPOSABLE PENILE ADJUSTABLE CONSTRICTION DEVICE

[76] Inventor: Pacifico R. Burgos, 721 E. Maple St., Glendale, Calif. 91205

[21] Appl. No.: 747,206

[22] Filed: Nov. 12, 1996

Related U.S. Application Data

[60] Provisional application No. 60/026,812 Sep. 27, 1996.
[51] Int. Cl.[6] ....................................................... A61F 5/00
[52] U.S. Cl. .................................. 600/41; 600/38; 600/39
[58] Field of Search .................................. 600/39, 41, 38; 128/883, 95.1

[56] References Cited

U.S. PATENT DOCUMENTS 5,027,800   7/1991   Rowland ..................................... 600/39

FOREIGN PATENT DOCUMENTS 107693   10/1967   Germany ................................... 600/41
734394    7/1955   United Kingdom ..................... 600/41

*Primary Examiner*—John P. Lacyk
*Assistant Examiner*—Rosiland Kearney
*Attorney, Agent, or Firm*—Robert M. Sperry

[57] ABSTRACT

A disposable penile erection enhancing constriction device comprising a split ring having a releasable fastening means for adjusting the constrictive effect of said device on the superficial veins around the base of the human penile organ. Said device can be provided in plurality of sizes to accommodate the wide variation in the sizes of the human penile organ.

9 Claims, 2 Drawing Sheets

DISPOSABLE PENILE ADJUSTABLE CONSTRICTION DEVICE

RELATED CASES

This application covers the invention disclosed in my Provisional patent application Ser. No. 60/026,812, filed on Sep. 27, 1996.

FIELD OF INVENTION

This invention relates to penile constriction devices and is particularly directed to penile erection enhancing constriction rings which are adjustable to enable the user to readily vary the amount of penile constriction and releasable to allow for its easy disposal.

PRIOR ART

Normal penile erection is initiated when a sexually stimulated person's brain sends signal through his spinal cord for his nerves to release neurotransmitters to relax the smooth muscles in the walls of the arterial network located mainly in the corpora cavernosa, deep in the penile organ. Likewise, during sexual excitement, the endothelial cells lining the lacunar spaces comprising the corpora cavernosa release chemical agents that either contract or relax the smooth muscled-walls of the lacunar spaces.

The relaxation of the smooth muscled-walls of the arterial network induces the blood to flow from the human heart to the penile organ. The relaxation of the smooth muscled-walls of the lacunar spaces, on the other hand, allows these spaces to expand and be filled up with blood brought in by the arterial network.

As sexual arousal heightens, the increasing volume of accummulated blood in the lacunar spaces compresses the subtunical venules against the tunica albuginea that encases the corpora cavernosa. This compressing effect on the subtunical venules limits them from draining the blood out of the penile organ. Thus, the continued inflow of the blood into the organ accummulates to a volume that limits the subtunical venules from draining the blood out—resulting to the swelling of the corpora cavernosa to full capacity at a prolonged duration. This is the ideal normal erection—maximum penile size and long-lasting.

Most men, even with normal erection however, do not always attain this ideal erection. This happens when a person engaging in sex is not sexually stimulated enough to be able to attain and prolong the highest level of arousal. In such case, the inflow of blood into his penis is not fast enough to accummulate to the volume that would naturally create the compressing effect on his subtunical venules. Thus, the subtunical venules are able to immediately drain the blood out of the penile organ before it accummulates to a significant volume. This results to smaller-sized and short lasting erection.

To overcome this problem, many men resort to surgical implants, others take medications and a lot more inject drugs into their organs. A great number of men however, purchase these expensive vacuum-constriction devices that are designed to induce and sustain maximum penile erection. These devices consist of a vacuum pump having a cylinder into which the penis is inserted. The device then creates a vacuum inside the cylinder, thereby inducing the blood to flow into the organ. To maintain the erection, heavy elastic rings are slipped off the cylinder and into the base of the penis to encircle and constrict the organ, hence prolonging the erection.

By nature, the human penile organ however, come in a very wide variety of sizes. Because they rely upon elasticity to provide the necessary constriction, the said elastic rings are provided in "one-size-fits-all" manner and thus, are very small in diameter. Therefore, when positioned on the penile organ, these elastic rings are extremely painful and often preclude the user from ejaculating and receiving any sensory feelings from the organ during sexual activity. Further, these rings do not allow for easy release and thus, forces the user to wait until his penis get limp before he is freed of the painful constriction.

There is therefore, a need for an inexpensive yet better device that will enable the user to have an enhanced erection and that which is easy and comfortable to use and do not preclude the user from normal ejaculation and penile sensory functions.

This pressing need is what the present invention intends to satisfy.

BRIEF SUMMARY OF THE INVENTION

The principal objective of the present invention is to provide a better yet inexpensive device that will enable the user to effectively and comfortably attain bigger and longer-lasting penile erection.

Accordingly, it is the specific objective of the invention to provide a device that will allow the user to optimally constrict the superficial veins around the base of his penis, thereby restricting the flow of blood from his penis back to his body during erection.

It is also an object ot the invention to provide two preferred forms of the said device in several size categories to accommodate the wide variety of human penile sizes.

It is a further object of the invention to provide a device having a means for the user to readily adjust the size of the said device for it to comfortably fit his own penile size.

It is likewise an object of the invention to provide a device having means for the user to easily adjust the degree of constriction effected by the device on his penis for comfort and unhampered ejaculation and penile sensory function.

It is also an object of the invention to provide a device having means for the user to readily fasten the said device on his penis and to release same device from his penis for disposal.

The foregoing objectives of the present invention are attained by providing a device comprising a split ring preferably of rigid yet resilient material such as soft plastic, hard rubber and the like. Said ring will have a fastening means comprising of interlocking parts to allow the user to adjust the size of the device to fit and be secured on his penis, to vary the amount of penile constriction for enhanced erection, and to enable him to release said ring from his penis for disposal.

The said objectives can further be fulfilled by having aforesaid device in several forms, with each form preferably having enlargements formed on the lower portion of the inner surface of the said ring for further penile constriction effect and same forms of the device desirably made in several size categories to accommodate the wide variation of sizes of the human penile organ.

These and other objects and embodiments of the present invention will be apparent in the following detailed description, discussed with reference to the figures in the related drawings.

DETAILED DESCRIPTION OF THE INVENTION

Figure 1:
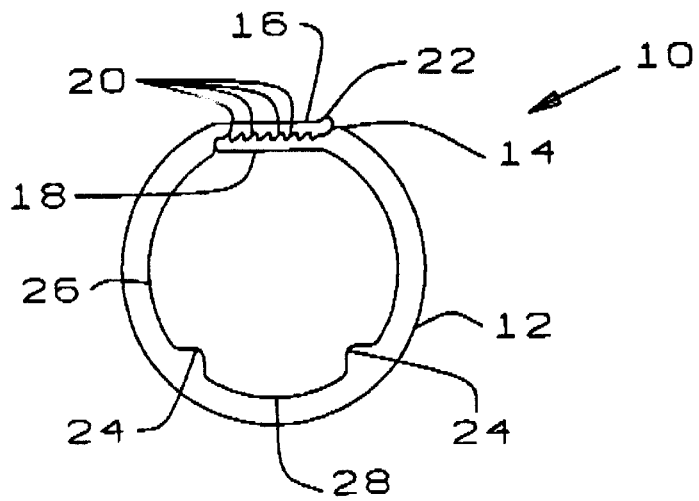
FIG. 1 is a front view of the disposable penile constriction device embodying the present invention.
Figure 2:
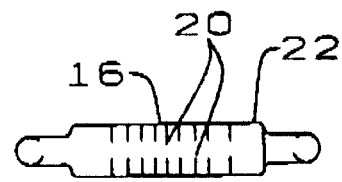
FIG. 2 is a top view of the penile constriction device of FIG. 1.

FIG. 1 shows that form of the present invention, which is taken for purposes of illustration, of a penile constriction device, indicated generally at 10, is shown comprising a ring 12 composed preferably of rigid yet resilient material, such as soft plastic, hard rubber and the like, having a desirably rounded circumference to enable the ring 12 to be comfortably placed about the base of the penile organ, not shown.

The ring 12 is split, preferably along its upper portion that may be enlarged, as seen at 14, and has overlapping portions 16 and 18 that can be opened apart to allow the ring 12 to be wrapped around the penis, not shown, when being set for use. The overlapping portions 16 and 18 form the adjustable and releasable fastening means, each overlapping portion 16 and 18 having interlockable parts 20. If desired, tab 22 may be provided adjacent the end of the overlapping portion 16 to facilitate the release and movement of the overlapping portions 16 and 18 with respect to each other. The ring 12 will preferably have two rounded enlargements 24 formed on the inner surface 26 adjacent the bottom part 28 of the ring 12. These two rounded enlargements 24 are intended to further constrict the lower portions of the corpora cavernosa of the penile organ.

In use, the ring may be provided in a plurality of sizes, such as small, medium and large, to enable each size to accommodate a variety of penile sizes within a general range determined by the size designation. The user, upon determining his desired ring size, can place the ring 12 on his penile organ before full erection, preferably having the overlapping portions 16 and 18 oriented towards his heart, by separating the overlapping portions 16 and 18 with respect to each other to easily set the ring 12 around the base of his penis.

The user can readily adjust the degree of penile constriction, provided by the diameter of the inner surface 26 and the two rounded enlargements 14 of ring 12, by moving the overlapping portions 16 and 18 towards or away from each other. Hence, if the user wants to increase the penile constriction of ring 12, he may move overlapping portion 16 toward overlapping portion 18. Reversely, if the user wants to decrease the penile constriction of ring 12, he may move both overlapping portions 16 and 18 away from each other. To fasten ring 12 on his penis, the user may engage the respective interlocking parts 20 of the overlapping portions 16 and 18, by pressing both portions 16 and 18 against each other. To unfasten and dispose of ring 12, the user may disengage the respective interlocking parts 20 of the overlapping portions 16 and 18 by pulling tab 22 until overlapping portions 16 and 18 separate from each other.

Figure 3:
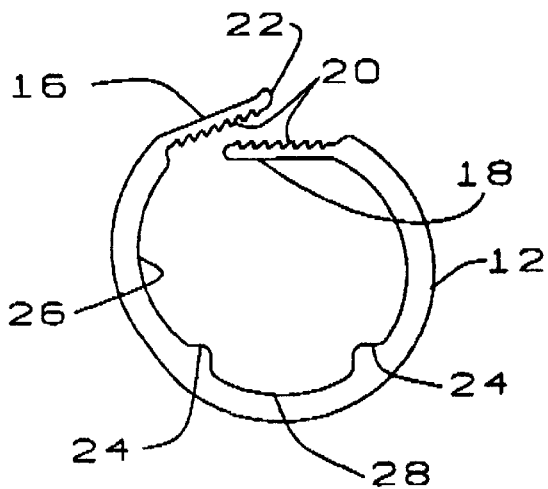
FIG. 3 is a view, similar to that of FIG. 1, showing the parts of the penile constriction device of FIG. 1 in spaced relation.
Figure 4:
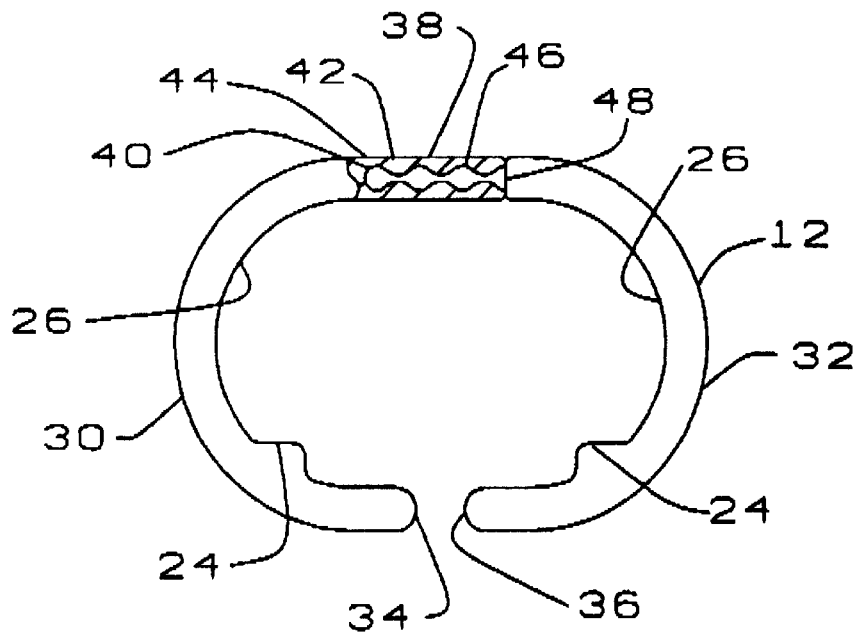
FIG. 4 is a front view, partly in section, showing an alternative form of the penile constriction device of FIG. 1.
Figure 5:
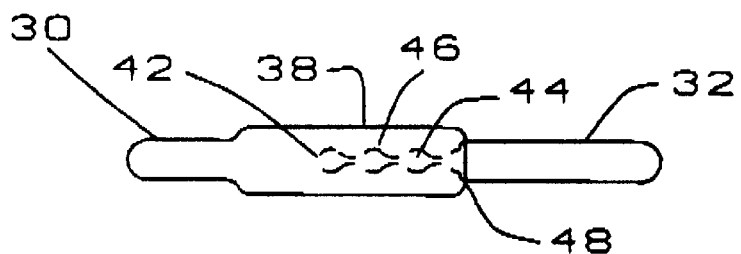
FIG. 5 is a top view of the penile constriction device of FIG. 3.
Figure 6:
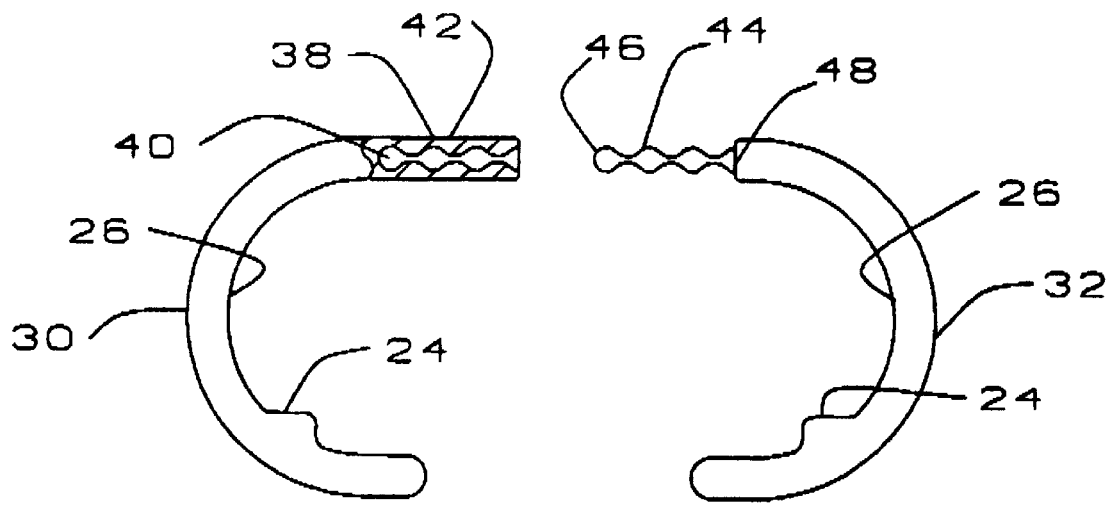
FIG. 6 is a view, similar to that of FIG. 4, showing the parts of the penile constriction device of FIG. 4, in spaced relation.

FIGS. 3–5 show an alternative form of the penile constriction device 10 comprising a ring 12 formed of a pair of generally C-shaped members 30 and 32, each desirably having an enlargement 24 formed on the inner surface 26 thereof, adjacent the lower ends 34 and 36 of members 30 and 32. The upper portion 38 of member 30 is formed with a recess 40 having a plurality of interior ridges 42 projecting inwardly along the recess 40. The upper portion of C-shaped member 32 is formed with a desirably rounded projection 44 having a plurality of external ridges 46 formed thereon which are interlockingly engageable with the ridges 42 of recess 40 of C-shaped member 30.

In use, projection 44 of C-shaped member 32 can be inserted into recess 40 of C-shaped member 30 to form ring 12 of the penile constriction device 10, as seen in FIG. 3, and can be moved inward or outward to obtain the desired diameter for the ring 12. To release the device from the penile organ, the user can gently pull apart member 30 from member 32 until the device 10 breaks at indented neck 48 of member 32.

Obviously, numerous other variations and modifications can be made without departing from the spirit of the present invention. Therefore, it should be clearly understood that the forms of the present invention as described herein and as shown in the figures of the accompanying drawings are illustrative only and are not intended to limit the scope of the present invention.

What is claimed is:

1. A penile constriction device comprising:

a split ring extendable about the base of a human penile organ having overlapping free ends with relealeasable fastening means carried by each of said ends and mateable with similar means carried by the opposite one of said ends to form releasable fastening means for said ends to provide adjustable constriction of the superficial veins around the base of a human penile organ.

2. The device of claim 1 wherein:

said releasable fastening means comprises interlocking parts formed on said overlapping free ends of said ring for adjusting the diameter of same ring.

3. The device of claim 1 wherein:

at least one of said overlapping free ends of said ring carries an outwardly projecting tab to facilitate movement of same overlapping free ends for size adjustment, for securing to or removal of same ring from the penile organ.

4. The device of claim 1 wherein:

said ring has an inner surface with enlargements formed on the lower portions of said inner surface to provide further constriction on the lower portion of the corpora cavernosa of the penile organ.

5. The device of claim 1 wherein:

said ring is formed of rigid yet resilient rounded material.

6. The device of claim 1 wherein:

said releasable fastening means comprise a plurality of alternate ridges and recesses.

7. The device of claim 1 wherein:

said ring is alternatively composed of a pair of generally C-shaped members hingedly joined to form said split ring.

8. The device of claim 7 wherein:

one of said C-shaped members with an upper-end portion having an internally ridged recess and the other of said C-shaped members with an upper-end portion having an externally ridged projection interlockingly engageable with said recess to adjust the diameter of said ring.

9. The device of claim 8 wherein:

said externally ridged projection having an indentation to facilitate breaking of said ring for release from the penile organ when the said C-shaped members are pulled apart for disposal.

* * * * *